(12) United States Patent
Osorio et al.

(10) Patent No.: US 11,672,431 B2
(45) Date of Patent: *Jun. 13, 2023

(54) SEIZURE DETECTION METHODS, APPARATUS, AND SYSTEMS USING AN AUTOREGRESSION ALGORITHM

(71) Applicant: Flint Hills Scientific, L.L.C., Lawrence, KS (US)

(72) Inventors: Ivan Osorio, Leawood, KS (US); Alexey Lyubushin, Moscow (RU); Didier Sornette, Zurich (CH)

(73) Assignee: FLINT HILLS SCIENTIFIC, L.L.C., Lawrence, KS (US)

( * ) Notice: Subject to any disclaimer, the term of this patent is extended or adjusted under 35 U.S.C. 154(b) by 676 days.

This patent is subject to a terminal disclaimer.

(21) Appl. No.: 16/706,688

(22) Filed: Dec. 7, 2019

(65) Prior Publication Data

US 2020/0107735 A1 Apr. 9, 2020

Related U.S. Application Data

(62) Division of application No. 13/559,116, filed on Jul. 26, 2012, now Pat. No. 10,537,251.

(Continued)

(51) Int. Cl.
| | |
|---|---|
| *A61B 5/00* | (2006.01) |
| *A61B 5/0205* | (2006.01) |
| *A61B 5/16* | (2006.01) |
| *A61B 5/374* | (2021.01) |
| *A61B 5/024* | (2006.01) |

(Continued)

(52) U.S. Cl.
CPC ........ *A61B 5/02055* (2013.01); *A61B 5/0205* (2013.01); *A61B 5/165* (2013.01); *A61B 5/374* (2021.01); *A61B 5/4094* (2013.01); *A61B 5/4836* (2013.01); *A61B 5/726* (2013.01); *A61B 5/746* (2013.01); *A61B 5/024* (2013.01); *A61B 5/0816* (2013.01); *A61B 5/0833* (2013.01); *A61B 5/1118* (2013.01); *A61B 5/14542* (2013.01); *A61B 5/16* (2013.01); *A61B 5/24* (2021.01); *A61B 5/369* (2021.01)

(58) Field of Classification Search
CPC .............. A61B 5/02055; A61B 5/0205; A61B 5/4094; A61B 5/4836; A61B 5/726; A61B 5/746; A61N 1/36128
See application file for complete search history.

(56) References Cited

U.S. PATENT DOCUMENTS 10,537,251 B2 * 1/2020 Osorio ................. A61B 5/0205

* cited by examiner

*Primary Examiner* — Unsu Jung
*Assistant Examiner* — James Moss
(74) *Attorney, Agent, or Firm* — CF3; Stephen Eisenmann

(57) ABSTRACT

A method, comprising receiving a time series of patient body signal, determining first and second sliding time windows for the time series; applying an autoregression algorithm, comprising: applying an autoregression analysis to each of the first and second windows, yielding autoregression coefficients and a residual variance for each window; estimating a parameter vector for each window based on the autoregression coefficients and residual variances; and determining a difference between the parameter vectors; and determining seizure onset and seizure termination based on the difference between the parameter vectors. A non-transitory computer readable program storage unit encoded with instructions that, when executed by a computer, perform the method.

7 Claims, 11 Drawing Sheets

Related U.S. Application Data

(60) Provisional application No. 61/547,567, filed on Oct. 14, 2011.

(51) Int. Cl.
*A61B 5/08* (2006.01)
*A61B 5/11* (2006.01)
*A61B 5/24* (2021.01)
*A61B 5/369* (2021.01)
*A61B 5/083* (2006.01)
*A61B 5/145* (2006.01)

SEIZURE DETECTION METHODS, APPARATUS, AND SYSTEMS USING AN AUTOREGRESSION ALGORITHM

The present application claims priority to and is a divisional application of U.S. Ser. No. 13/559,116, filed on Jul. 26, 2012 entitled "SEIZURE DETECTION METHODS, APPARATUS, AND SYSTEMS USING A SHORT TERM AVERAGE/LONG TERM AVERAGE ALGORITHM", which claims priority to U.S. provisional patent application Ser. No. 61/547,567, filed on Oct. 14, 2011, which are both incorporated in their entireties herein by reference.

BACKGROUND OF THE INVENTION

1. Field of the Invention

The present invention relates generally to the field of epileptic event detection. More particularly, it concerns epileptic event detection by use of an autoregression algorithm on a time series of patient body signal data.

2. Description of Related Art

There have been various advancements in the area of seizure detection, which remains a fairly subjective endeavor. The task of automated detection of epileptic seizures is generally related to and dependent on the definition of what is a seizure, definition which to date is subjective and thus inconsistent within and among experts. The lack of an objective and universal definition complicates not only the task of validation and comparison of detection algorithms, but also (and possibly more importantly), the characterization of the spatio-temporal behavior of seizures and of other dynamical features required to formulate a comprehensive epilepsy theory.

The current state of automated seizure detection is, by extension, a reflection of the power and limitations of visual analysis, upon which it rests. The subjectivity intrinsic to expert visual analysis of seizures and its incompleteness (it cannot adequately quantify or estimate certain signal features, such as power spectrum) confound the objectivity and reproducibility of results of signal processing tools used for automated seizure detection. What is more, several of the factors that enter into the determination of whether or not certain grapho-elements should be classified as a seizure are non-explicit ("gestalt-based") and thus difficult to articulate, formalize and program into algorithms.

Most, if not all, existing seizure detection algorithms are structured to operate as expert electroencephalographers. Thus, seizure detection algorithms that apply expert-based rules are at once useful and deficient; useful as they are based on a certain fund of irreplaceable clinical knowledge, and deficient as human analysis biases propagate into their architecture. These cognitive biases which pervade human decision processes and which have been the subject of formal inquiry are rooted in common practice behaviors such as: a) The tendency to rely too heavily on one feature when making decisions (e.g., if onset is not sudden, the event is unlikely to be characterized as a seizure because seizures are paroxysmal events); b) To declare objects as equal if they have the same external properties (e.g., this is a seizure because it is just as rhythmical as those we score as seizures) or c) relying on the ease with which associations come to mind (e.g., this pattern looks just like the seizures we reviewed yesterday).

Seizure detection algorithms' mixed results make attainment of a unitary or universal seizure definition ostensibly difficult. In addition to cognitive biases, the inadequacy of many seizure detection algorithms may also be attributable in part, to the distinctiveness in the architecture and parameters of each algorithm. The fractal or multi-fractal structures of seizures accounts at least in part for the differences in results, and draws attention to the so-called "Richardson effect." Richardson demonstrated that the length of borders between countries (a natural fractal) is a function of the size of the measurement tool, increasing without limit as the tool's size is reduced. Mandelbrot, in his seminal contribution "How long is the coast of Britain," stressed the complexities inherent to the Richardson effect, due to the dependency of particular measurements on the scale of the tool used to perform them. Although defining seizures as a function of a detection tool would be acceptable, this approach may be impracticable when comparisons between, for example, clinical trials or algorithms are warranted. Another strategy to bring unification of definitions is to universally adopt the use of one method, but this would be to the detriment of knowledge mining from seizure-time series and by extension to clinical epileptology.

To date, meaningful performance comparisons among myriad existing algorithms have not been feasible due to lack of a common and adequate database. However, even if adequate databases were available, the value of such "comparisons" would be limited by the absence of a universally accepted definition of what is a "seizure." The previously noted cognitive biases and architectural/parametric distinctions among algorithms impede achievement of consensus and in certain cases even of majority agreement in classifying particular events as seizures or non-seizures. Because expert visual analysis provides the benchmarks (seizure onset and termination times) from which key metrics (detection latency in reference to electrographic and clinical onset time ("speed of detection"), sensitivity, specificity and positive predictive value) are derived, the effects of cognitive biases propagate beyond the seizure/non-seizure question into other aspects of the effectiveness of a particular seizure detection algorithm.

SUMMARY OF THE INVENTION

In one embodiment, the present disclosure provides a method, comprising: receiving a time series of a first body signal of a patient, determining a first sliding time window and a second sliding time window for said time series of said first body signal;

applying an autoregression algorithm, comprising: applying an autoregression analysis to each of said first and second windows to yield a plurality of autoregression coefficients for each said window and a residual variance for each said window; estimating a parameter vector for each of said first and second windows, based at least in part on said autoregression coefficients and said residual variances; and determining a difference between said parameter vectors for said first and second windows using a matrix function;

determining an onset of a seizure based on said difference between said parameter vectors, wherein said difference indicates a larger variance in said second window than in said first window; and determining a termination of a seizure based on said difference between said parameter vectors, wherein said difference indicates a larger variance in said first window than in said second window.

In one embodiment, the present disclosure provides a non-transitory computer readable program storage unit encoded with instructions that, when executed by a computer, perform a method as described above and herein.

BRIEF DESCRIPTION OF THE DRAWINGS

The invention may be understood by reference to the following description taken in conjunction with the accompanying drawings, in which like reference numerals identify like elements, and in which.

Figure 1:
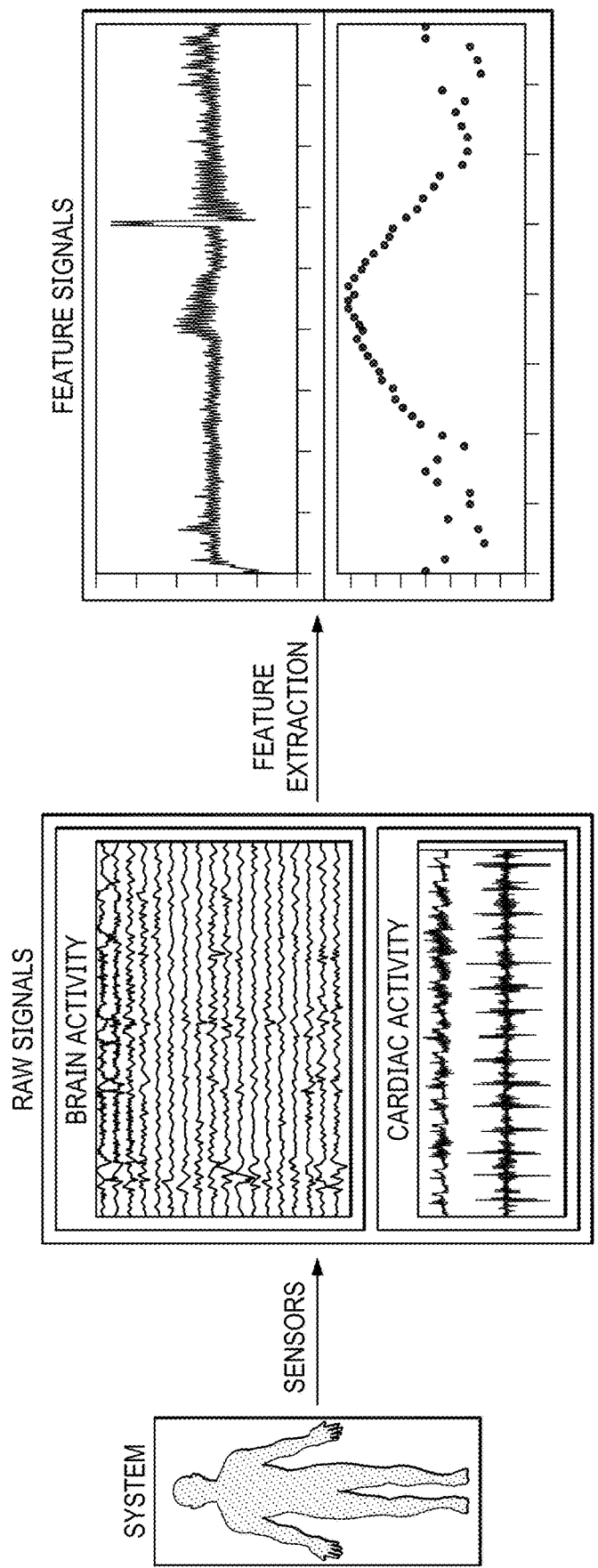
FIG. 1 illustrates a medical device system for detecting and classifying seizure events related to epilepsy from sensed body data processed to extract features indicative of aspects of the patient's epilepsy condition.

DESCRIPTION OF ILLUSTRATIVE
EMBODIMENTS

In one aspect, the present disclosure provides several new seizure detection algorithms that may be applied to one or more streams of body data. Some of these algorithms rely principally on power variance for detection of seizures, while others rely mainly on power spectral shape.

In another aspect, the present disclosure exploits the simultaneous application of two or more individual seizure detection algorithms to derive a probabilistic measure of seizure activity (PMSA), which may be used to issue detections by majority or consensus of a plurality of the two or more seizure detection algorithms, depending on safety factors and others such as detection speed, sensitivity, specificity or any other performance measures and the clinical application(s) at hand. Real-time ("on the run") automated seizure detection provides the only means through which contingent warning to minimize risk of injury to patients, delivery of a therapy for control of seizures, or logging of the date, time of onset and termination and severity may be performed.

This disclosure, in one embodiment, provides an autoregression algorithm suitable for use in epileptic event detection, by operation on a time series of patient body signal data. Such an autoregression algorithm may be used by itself, or as part of a Probabilistic Measure of Seizure Activity.

More generally, this disclosure: a) draws attention to the complexities inherent to the pursuit of a universal seizure definition even when powerful, well understood signal analysis methods are utilized; b) identifies this aim as a multi-objective optimization problem and discusses the advantages and disadvantages of adopting or rejecting a unitary seizure definition; c) introduces a Probabilistic Measure of Seizure Activity to manage this thorny issue.

Seizure detection belongs to a class of optimization problems known as "multi-objective" due to the competing nature between objectives: improvements in specificity of detection invariably degrade sensitivity, and vice-versa. Attempts to achieve a universal seizure definition using objective, quantitative means are likely to be fraught with similar competing objectives. In one aspect, the present invention involves the application of tools from the field of multi-objective optimization, among others to make the problems caused by competing objectives more tractable.

Achieving a unitary seizure definition would be difficult, as consensus among epileptologists as to what graphoelements are classifiable as ictal, is rare. In the absence of a universal definition, issuing seizure warnings for certain cases will be problematic and unsafe. For example, if a patient with seizures wishes to operate power equipment or a motor vehicle, the absence of a universal agreement on when the patient has had a seizure may preclude any viable way of ensuring, using seizure detection algorithms, that the patient's seizures are under sufficient control to allow such activities to occur. To manage the difficulties of a consensus seizure definition, substantive gains are feasible through steps entailing, for example, the application of advanced signal analysis tools to ECoG, to hasten the identification of properties/features that would lead to the probabilistic discrimination of seizures from non-seizures with worthwhile sensitivity and specificity for the task at hand. However, to even have a modicum of success, such an approach should not ignore the non-stationarity of seizures and, should strike some sort of balance between supervised (human) and unsupervised machine-learning) approaches. The resulting multidimensional parameter space, expected to be broad and intricate, may also foster discovery of hypothesized (e.g. pre-ictal) brain sub-states.

The challenges posed by the attempt to define seizures unitarily using objective means (distinct from visual analysis) may be partly related to their fractal properties and understood through a simplistic analogy to the so-called "Richardson effect". A revision of the time-honored subjective definition of seizures may be warranted to further advance epileptology.

In one aspect, the present disclosure provides a Probabilistic Measure of Seizure Activity (PMSA) as one possible strategy for characterization of the multi-fractal, non-stationary structure of seizures, in an attempt to overcome the more substantive limitations intrinsic to other seizure detection methods, including those involving scalp or even direct brain recordings of electrical activity.

The PMSA may make use of "indicator functions" (IFs) denoted $\chi_{algo}$ for each algorithm. In one embodiment, the PMSA may also make use of an Average Indicator Function (AIF). In one embodiment, the AIF is defined as:

$$\text{AIF}(t)=(\chi_{Val}(t)+\chi_{r^2}(t)+\chi_{STA/LTA}(t)+\chi_{WTMM}(t))/4$$

The subscripts Val, $r^2$, STA/LTA and WTMM refer to four different seizure detection algorithms, particular embodiments of which are described herein and/or in other related applications. One or more of these algorithms may be used to detected seizures from one or more body data streams including, but not limited to, a brain activity (e.g., EEG) data stream, a cardiac (e.g., a heart beat) data stream, and a kinetic (e.g., body movement as measured by an accelerometer) data stream. "Val" refers to an algorithm for seizure detection using ECoG data that has been validated by experts without reaching a universal consensus about its performance (e.g., false positive, false negative and true positive detections). An "$r^2$" algorithm may also be referred to herein as an "$r^2$," "autoregression," or "autoregressive" algorithm. A STA/LTA algorithm refers to an algorithm characterized by the ratio of a Short-Term Average to a Long-Term Average. A WTMM algorithm refers to a Wavelet Transform Maximum Modulus algorithm.

For determination of an AIF from the foregoing formula, an algorithm's IF (i.e., output values for each of $\chi_{Val}$, $\chi_{r2}$ $\chi_{STA/LTA}$, and $\chi_{WTMM}$) equals 1 for time intervals (0.5 sec in this application) "populated" by ictal activity and 0 for time intervals populated by inter-ictal activity. The IF's are used to generate four stepwise time functions, one for each of: a) a $2^{nd}$ order auto-regressive model ($r^2$); b) the Wavelet Transform Maximum Modulus (WTMM) model; and c) the ratio of short-to-long term averages (STA/LTA) and d) a Validated algorithm (Val). From the indicator functions determined for the individual algorithms, the average indicator function (AIF is computed. In one embodiment, the AIF may range between [0-1], with intermediate values of 0.25, 0.5 and 0.75. Intermediate AIF values may be a function of the number of algorithms applied to the signal. Where, for example, 4 algorithms are used and the range of the indicator function is [0-1], the intermediate values are [0.25, 05, 0.75]). These values [0-1] are estimates of the probability of seizure occurrence at any given time. In another embodiment, the values of each algorithm's IF may be weighted differently, and a composite IF (e.g., a Weighted Indicator Function or WIF) different from the AIF may be computed.

Data obtained from a subject undergoing evaluation for epilepsy surgery with intracranial electrodes was selected for analysis. The ECoG was recorded using electrodes implanted into the amygdala, pes hippocampus and body of hippocampus bilaterally through the temporal neocortex and had a duration of 6.9 days (142,923,853 samples; 239.75 Hz sampling rate).

Figure 11:
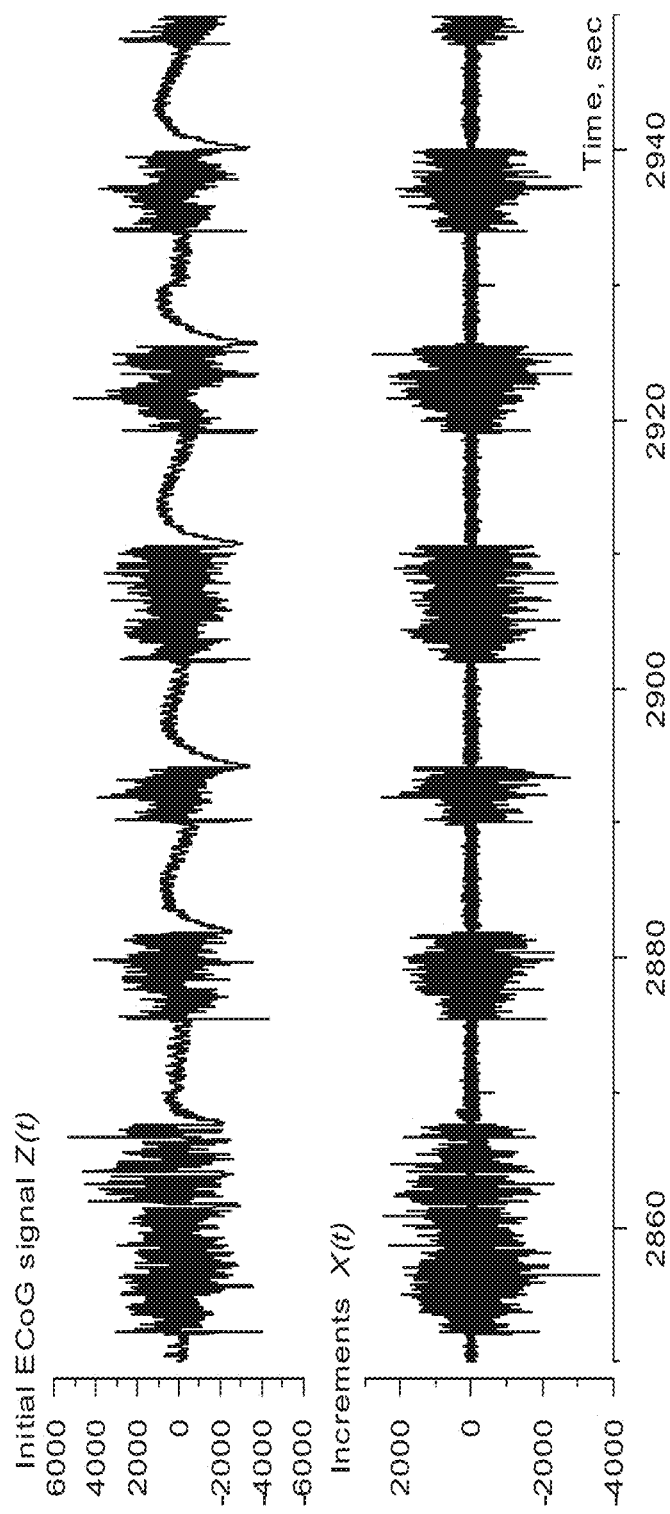
FIG. 11 shows ECoG before (upper panel) and after differentiation (lower panel), in accordance with one illustrative embodiment of the present disclosure.
Figure 12:
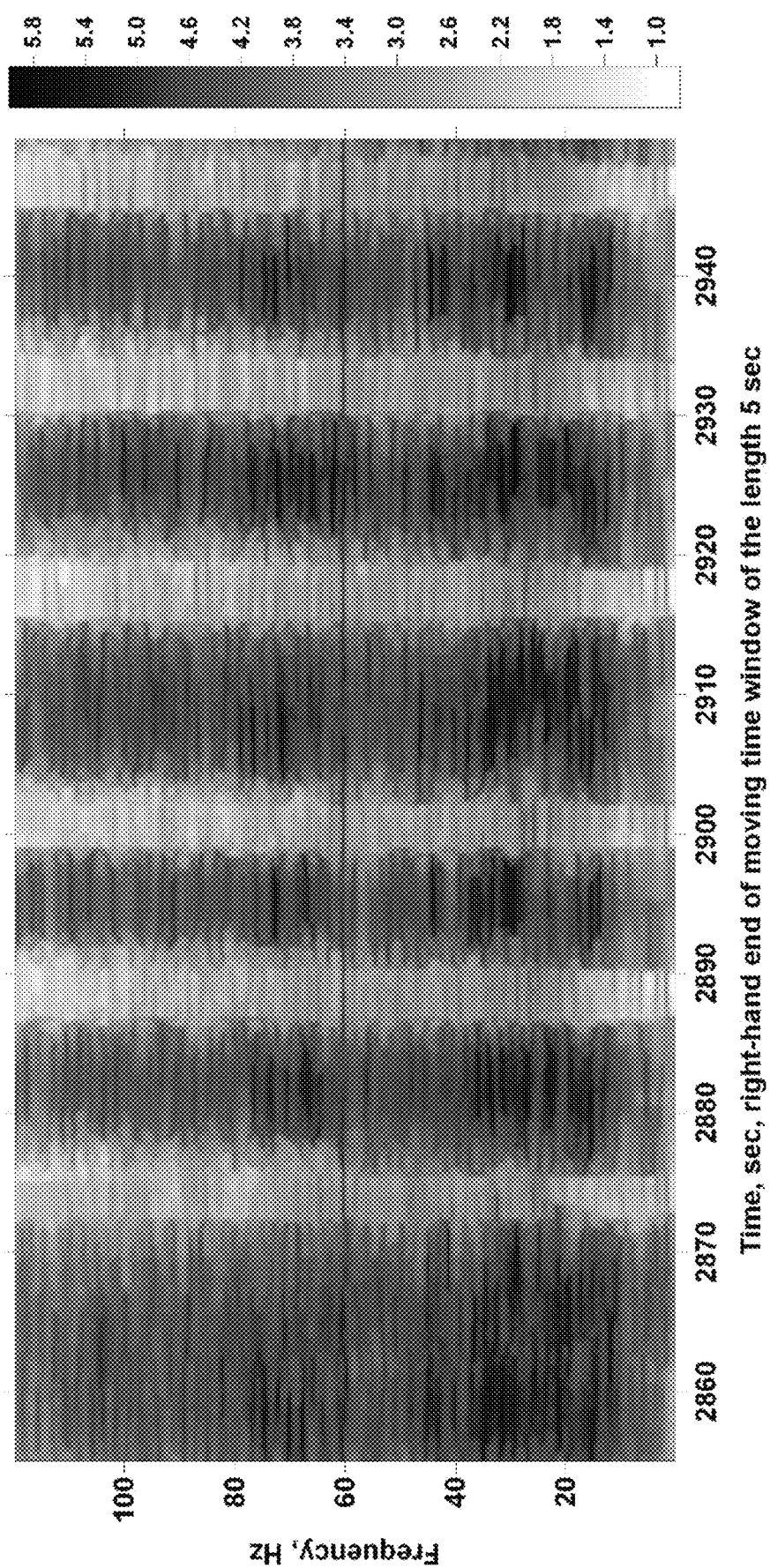
FIG. 12 shows temporal evolution of the decimal logarithm of the power spectrum of differentiated ECoG.

For efficient analyses, ECoG signal differentiation was performed, so as to minimize the non-stationarity present in them. If Z(t) is raw ECoG, then its difference is X(t)=Z(t)–Z(t–1), where (t) corresponds to a sample time increment. This linear operation is exactly invertible and, unlike band-pass filtering or detrending, does not suppress low frequency fluctuations, but decreases their overall influence. FIG. 11 illustrates the effect of this operation on raw ECoG and FIG. 12, a time-frequency map of the evolution of the power spectra of differentiated ECoG segments. The power spectra are estimated within 5 sec moving windows of length.

Seizure Detection with the "$r^2$-Method"

Consider the autoregressive model of the p-th order for the signal increments:

$$X(t) + \sum_{k=1}^{P} a_k \cdot X(t-k) = d + \varepsilon(t), \quad (1)$$

$$M[\varepsilon(t)] = 0,$$

$$M[\varepsilon^2(t)] = \sigma^2$$

where $M[\bullet]$ is the symbol for a mathematical expectation. The model (1) can be re-written in a more compact form:

$$X(t)=c^T Y(t)+\varepsilon(t),\ Y(t)=(-X(t-1),\ldots,-X(t-p),1)^T,$$
$$c=(a_1,\ldots,a_p,d)^T \quad (2)$$

where $c^T Y(t)$ is a scalar product of column-vectors with $c^T$ being the transposed vector of c. Thus, in the AR-model, each sample is presented as a weighted sum of p previous values with weights given by the AR-coefficients, plus some shift d and the residual $\varepsilon(t)$, which is regarded as noise with zero mean value and variance $\sigma^2$. The full vector of parameters of the AR-model is $\theta=(c^T, \sigma)^T$.

A vector $\theta$ is estimated for each of the two moving time half-windows of equal length L to the left (background) and right (foreground) of the window's center $\tau$. Let $\theta^{(1)}$ be the left half-window parameter vector and $\theta^{(2)}$ the right half-window parameter vector, and $\Delta\theta=\theta^{(2)}-\theta^{(1)}$ their difference. Their difference is weighed using Fisher's matrix for the model (1) defined by:

$$B = -\frac{\partial^2 \ln(\Phi)}{\partial \theta \partial \theta}, \quad (3)$$

$$\ln(\Phi) = -(L-p)\ln(\sigma) - \frac{1}{2\sigma^2}\sum_t (X(t) - c^T Y(t))^2$$

Expression (3) defines B as the matrix constructed from the second-order derivatives of the logarithm of the likelihood function $\Phi$ under the assumption that $\varepsilon(t)$ is Gaussian white noise. Let $B^{(1)}$ and $B^{(2)}$ be the matrices (3) computed in the left and right halves of the moving time window and let us introduce, in one embodiment, a measure of non-stationarity:

$$r^2(\tau)=(\Delta\theta^T B^{(1)}\Delta\theta+\Delta\theta^T B^{(2)}\Delta\theta)/(2(L-p)) \quad (4)$$

This measure ($r^2$) provides a natural dimensionless estimate of the non-stationary behavior of the signal X(t). To make the calculation explicit, this equation (4) is estimated by using the following expression:

$$\Delta\theta^T B \Delta\theta = \frac{2(\Delta\sigma)^2}{\sigma^2} + \frac{\Delta c^T \left(\sum_i Y(t)Y^T(t)\right)\Delta c}{\sigma^2(L-p)} + \frac{4\Delta c^T \Delta\sigma \sum_i \varepsilon(t)Y(t)}{\sigma^3(L-p)} \quad (5)$$

The non-stationarity measures (4)-(5) will be used to identify the onset and termination of seizures based on the condition that a local maximum of $r^2$ exceeds a given threshold R. Specifically, if $$r^2(\tau) = \max_{\xi}\{r^2(\xi), \tau - L/4 \leq \xi \leq \tau + L/4\}, r^2(\tau) \geq R, \qquad (6)$$

then, the time $\tau$ is
1. the onset of a seizure if $\sigma_2 > \sigma_1$ (the variance of the residuals of the AR process is larger in the right half of the window (foreground) than in the left half (background);
2. the termination of a seizure if $\sigma_1 > \sigma_2$ (the variance of the residuals of the AR process is smaller in the right half of the window than in the left half).

Condition (6) reflects the large non-stationarity present in the signal associated with the onset or termination of seizures as determined by the jumps from low to high variance (seizure onset) or vice-versa (seizure termination) at time $\tau$.

The values of the residual variances $\sigma_1$ and $\sigma_2$ are the parameters of the "$r^2$ Method" as well as components of the vector c, which is why they are consolidated into a general vector of parameters $\theta = (c^T, \sigma)^T$. The method is based on comparing vectors $\theta_1$ (left half-window) and $\theta_2$ (right-half window) using Fisher's matrix as a "natural" statistical metric. It is worth pointing out, that the AR(2) method is not sensitive to changes of variance in power, but to changes in the shape of the spectral density; this is because a short time window estimate $\hat{S}_{XX}(\omega)$ of the spectral density is directly connected with the vector of parameters $\theta$ by the equation $\hat{S}_{XX}(\omega) = \sigma^2/(2\pi \cdot |1 + a_1 e^{-i\omega} + a_2 e^{-2i\omega}|^2)$, where $\omega$ is a frequency and $i$ is the imaginary unit. This connection makes this method sensitive to changes in the auto-covariance function $R_{XX}(k) = M\{X(t)X(t-k)\}$ as follows from the Wiener-Khinchin theorem:

$$S_{XX}(\omega) = \sum_{k=-\infty}^{+\infty} R_{XX}(k) \cdot e^{-ik\omega}, \text{ where } R_{XX}(k) = \int_{-\pi}^{\pi} S_{XX}(\omega) \cdot e^{ik\omega} d\omega.$$

The AR, and validated algorithms have been described in U.S. provisional patent application Ser. No. 61/547,567, filed on Oct. 14, 2011, which is hereby incorporated by reference herein in its entirety.

The total number of detections, their duration and the percent time spent in seizure over the time series total duration (6.9 days) are presented in Table 1.

TABLE 1

|  | Validated algorithm | $r^2$ |
|---|---|---|
| Total number of seizures with duration ≥ 2 s. | 3184 | 7029 |
| Mean duration, s. | 3.8 | 23 |
| Median duration, s. | 3.4 | 7 |
| % time spent in seizure | 2 | 27 |

Summary statistics obtained by applying two different detection methods (Validated Algorithm; $r^2$). The minimum duration of seizures was set at 2 s.

Figure 6:
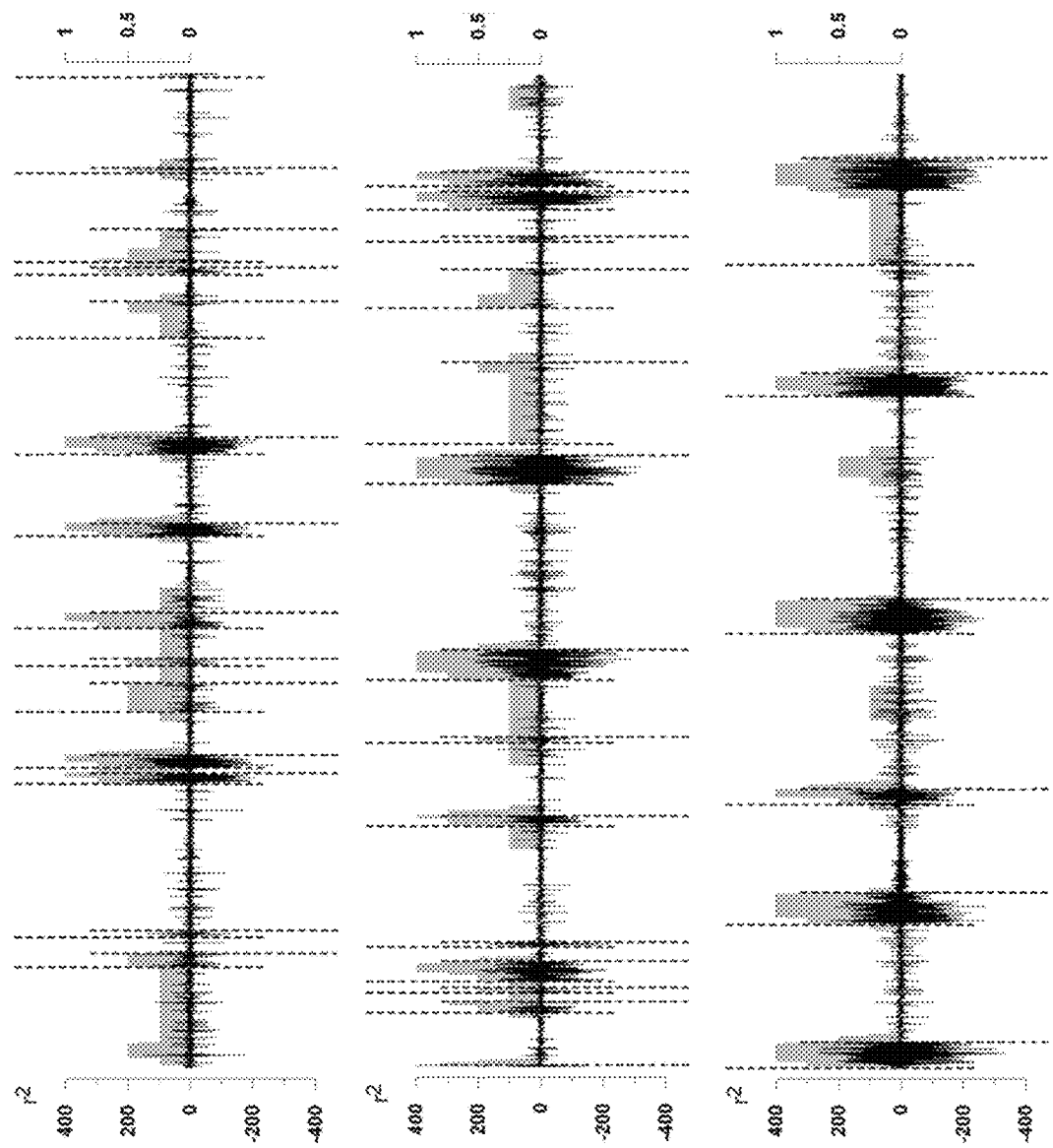
FIG. 6 illustrates the output of the $r^2$ algorithm in reference to an Average Indicator Function (AIF) making use of the output four algorithms, including the $r^2$ algorithm, in accordance with one illustrative embodiment of the present disclosure.

FIG. 6 illustrates the output of the $r^2$ algorithm in comparison with an average indicator function (AIF) making use of each of the validated algorithm, and the $r^2$ (AR), STA/LTA and WTMM algorithms. Specifically, FIG. 6 shows results of applying the $r^2$ seizure detection method to a differentiated ECoG (in black; 200 sec/panel) of a human with pharmaco-resistant epilepsy. The grey boxes represent the values (right y-axis) of an Average Indicator Function in the interval [0,1]. Seizure onset and end times are indicated by vertical lines (red for onset, blue for termination). Notice that the value of the Average Indicator Function is rarely 1 at either of the seizure onset or termination, indicating that all methods do not detect the ECoG activity as being ictal in nature at those moments. However, with seizures exceeding certain duration (at least 20 seconds) and intensity thresholds, they converge to all detect the seizure event. This indicates that the spectral and other properties of seizures are not homogeneous at the onset and termination of seizures, which is consistent with the lack of agreement among human experts (and algorithms) during onset and termination. Left y-axis: ECoG amplitude (in µV); excursions above zero correspond to positive, and below, to negative, polarity.

Table 2 provides further evidence that, at some point in time, the majority of seizures are detected by the validated algorithm are also detected by the other three methods, with WTTM detecting the largest number (97%) and STA/LTA the second largest (91.5%) number of seizures. More specifically and by way of example, the value 0.971 in Table 2 means that the WTMM method detections encompass 97.1% of seizure time intervals detected with the validated method, with the exception of 1.6 s. that correspond to the delay/lag between them in detecting seizure onsets (see below for details).

Time intervals for which the pairwise product $\chi_{Val}(t) \cdot \chi_{r^2}(t) = 1$ correspond to seizures detected by both the validated algorithm and the $r^2$ algorithm. Dividing the number of time intervals when $\chi_{Val}(t) \cdot \chi_{r^2}(t) = 1$ by the number of intervals when $\chi_{Val}(t) = 1$, yields the specificity of the $r^2$ method with respect to the validated algorithm. Since the validated algorithm has an inherent delay of 1 s and an additional duration constraint of 0.84 s. is imposed before a detection is issued, its onset and termination times are "delayed" compared to those yielded by the $r^2$ algorithm. To account for this delay and make comparisons more meaningful, the specificity of the $r^2$ with respect to the validated algorithm is re-calculated as a function of a time shift $\tau$:

$$Spe_{r^2\_Val}(\tau) = \sum_t (\chi_{r^2}(t+\tau) \cdot \chi_{Val}(t)) \Big/ \sum_t \chi_{Val}(t) \qquad (25)$$

The present inventors discovered that the time differences are negative for all three algorithms compared to the validated algorithm; that is, the validated algorithm's detection times lag behind those given by the other algorithms. More particularly, the mean delay of the validated algorithm is 1.1 s with respect to $r^2$, The re-calculated specificity values shifted by τ shown in Table 2 are higher compared to those without shifting.

TABLE 2

Values of specificity of the $r^2$, calculated with respect to the validated method, and time lag (as defined in the text) at which the specificity attains its largest value.

| Method | $Spe_{Method\_Val}(0)$ | $\max_{\tau} Spe_{Method\_Val}(\tau)$ | $\text{argmax}_{\tau} Spe_{Method\_Val}(\tau)$ |
|---|---|---|---|
| $r^2$ | 0.628 | 0.882 | −1.1 s |

Figure 7:
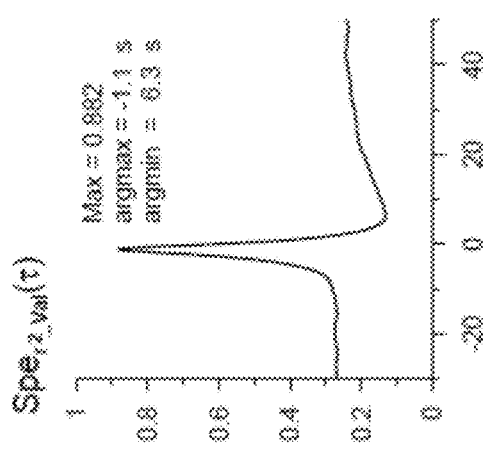
FIG. 7 shows a graph of a specificity function for the $r^2$ method as a function of time with respect to a validated algorithm's time of seizure detection, in accordance with one illustrative embodiment of the present invention.

The information in Table 2 is also depicted graphically in FIG. 7, which illustrates a graph of a specificity function for the $r^2$ method as a function of time with respect to the validated algorithm's time of seizure detection. Tau (τ) zero (x-axis) corresponds to the time at which the validated algorithm issues a detection. Negative τ values indicate "late" detections by the validated algorithm in relation to the $r^2$ algorithm and positive values the opposite. As shown, $r^2$ algorithm issues earlier detections than the validated algorithm. Values of the lags (τ) corresponding to the maximum and minimum values of the function are presented under the names argmax and argmin respectively.

The present inventors also discovered that only 45.3% of seizures recognized as such by the $r^2$ algorithm were also detected by the validated method, indicating that in its generic form and by design, the validated algorithm is less sensitive and more specific for seizure detection than the $r^2$ algorithm.

The $r^2$ method, along with the other methods mentioned supra, survey different but inter-dependent ECoG signal properties, thus expanding the breadth and perhaps also the depth of insight into the spectral "structure" of epileptic seizures in a clinically relevant manner. The Auto-Regressive model ($r^2$), which is implementable in a real-time embodiment, is sensitive mainly to changes in spectral shape, is the most general method of the algorithms previously mentioned (e.g., WTMM, STA/LTA) for providing a statistical description of oscillations (ECoG) that may be regarded as generated by the stochastic analogue of a linear oscillator.

Algorithmic and visual expert analysis consensus as to what grapho-elements define a seizure event seems to be highly dependent on when during the course of the event a detection decision is made. In this context, it is noteworthy that AIF frequently reached a value of 1, indicative of concordance among all detection methods, sometime after seizure onset and before its termination (as determined by any of the methods), provided the seizures reached a certain duration (20-30 s.) as discussed in more detail in U.S. provisional patent application Ser. No. 61/547,567, filed on Oct. 14, 2011. In short, seizure onsets and terminations may be under certain conditions universally undefinable by algorithmic or expert visual analysis. A systematic investigation of the differences in signal spectral properties between the "preface"/"epilogue" and the "main body" of seizures was not performed. It is speculated that the presence of "start-up transients" (in a dynamical sense) and of temporo-spatial dispersion of the ictal signal (which impacts S/N) may be most prominent at the onset and termination of seizures. These and local and global state-dependencies of certain signal features, account in part for the temporal fluctuations in algorithm detection performance.

Defining seizure energy as the product of the standard deviation of the power of ECoG by its duration (in seconds), reveals that the $r^2$ algorithm identifies as a continuum seizures that the validated algorithm detects as clusters of short seizures. The lack of correspondence between a certain percentage of detections (11.8% for the $r^2$ method) and the validated algorithm may be partially attributed to brief discontinuities in seizure activity as shown in FIG. 6. This phenomenon ("go-stop-go") appears to be inherent to seizures (e.g., it is a general feature of intermittency associated with many dynamical systems). These discontinuities are also an "artifact" caused by the architecture of and parameters used in each algorithm. For example, the longer the foreground window and the higher the order statistical filter (e.g., median vs. quartile), in the validated algorithm, the higher the probability that "gaps" in seizure activity will occur. Clustering of detections one a strategy to manage dynamical or artifactual ictal "fragmentation," and in this sense the $r^2$ algorithm avoids the subjective biases and arbitrariness associated with human-imposed clustering rules.

Figure 8:
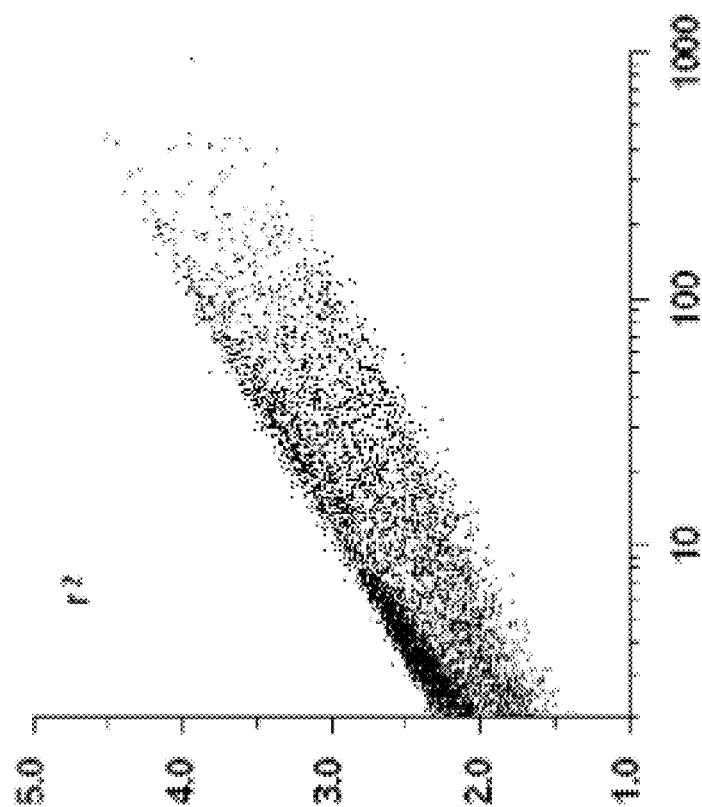
FIG. 8 shows a plot of the decimal logarithm of the dependence of seizure energy on seizure duration, in accordance with one illustrative embodiment of the present disclosure.

The dependencies of seizure energy (defined as the product of the standard deviation of the differentiated ECoG signal and seizure duration, in sec.) on seizure duration, for the set of icti detected by the $r^2$ method is depicted in FIG. 8. A subset of seizures detected by all methods obeys a simple law of proportionality between energy (y-axis) and duration (x-axis, log scale, seconds), that is, the longer the seizure, the larger its energy. However, this relationship is not invariably linear for other detection algorithms, indicating the presence of interesting scaling properties of seizure energy.

Figure 9:
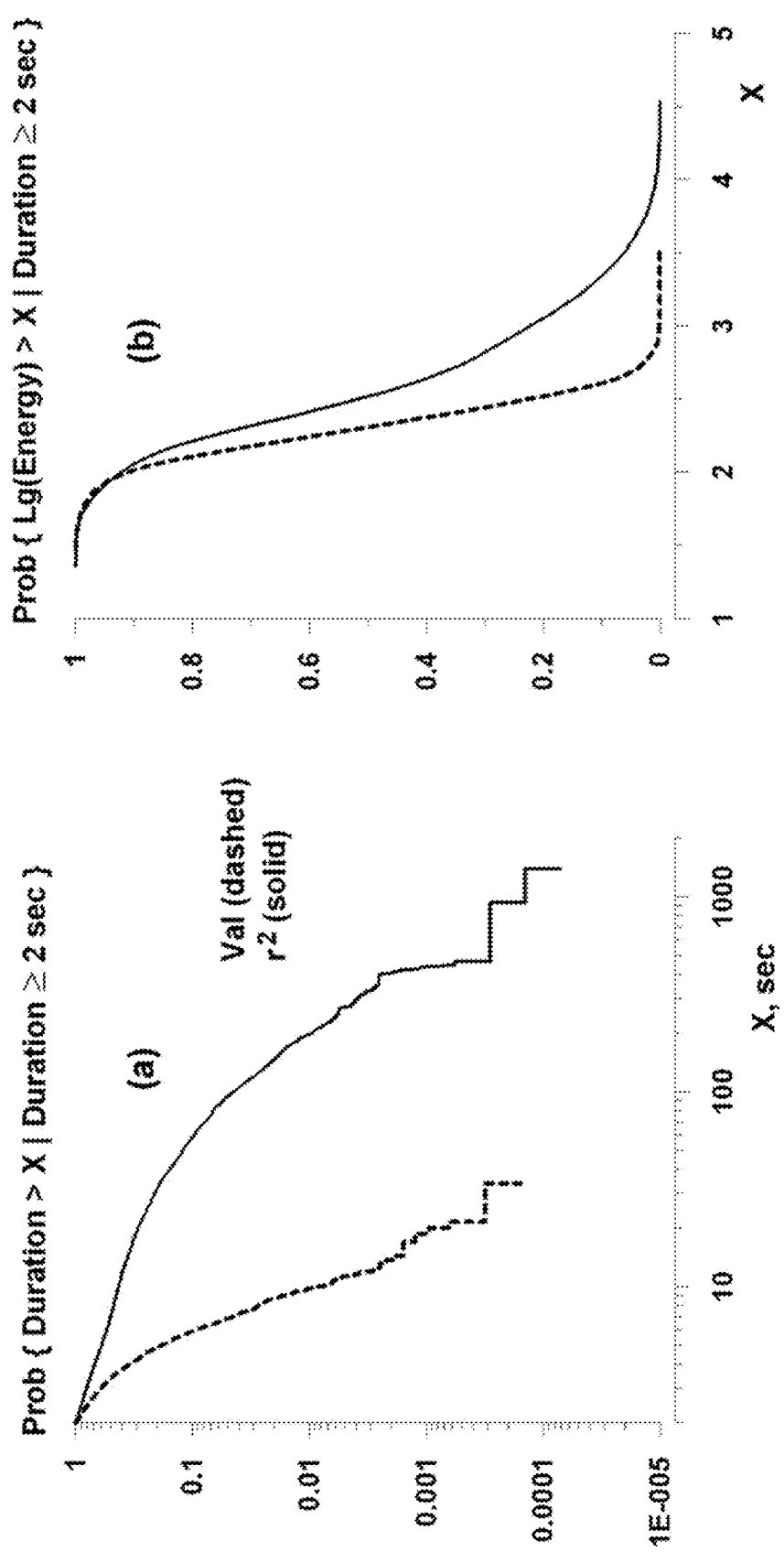
FIG. 9 shows the empirical "tail" of the conditional probability distribution functions for: (a) Seizure durations (minimum duration: 2 sec); and (b) the logarithm of seizure energy as estimated with four different methods, in accordance with one illustrative embodiment of the present disclosure.

FIG. 9 shows the empirical "tail" of the conditional probability distribution functions for: (a) Seizure durations (minimum duration: 2 sec); (b) the logarithm of seizure energy as estimated with the Validated method (solid) and the $r^2$ (Auto-regressive) method (dashed).

The conditional probabilities of durations (FIG. 9a) and of the logarithm of energy of seizures (FIG. 9b) provide additional support for the proposition that seizure properties are partly a function of the method used for their detection. The validated algorithm yields a different duration from the $r^2$ method. The distributions of the logarithm of seizure energies as identified by each of the methods (FIG. 9b) reveals additional discrepancies as evidenced by the much narrower and shorter "tail" distribution of the validated algorithm compared to the others.

The medical and psycho-socio-economic burden imposed upon patients, caregivers and health systems by pharmaco-resistant epilepsies is enormous. Intracranial devices for automated detection, warning and delivery of therapy, is a presently preferred "line of attack." However, reliance on extra-cerebral signals that are under cortical modulation or control (such as cardiac or motor activity) and are altered by seizures, emerges as a viable research direction with potentially fruitful clinical applications.

The greater ease of implementation and lower cost of automated real-time detection, warning and therapy systems based on extra-cerebral signals, compared to those requiring intracranial placement, makes them worthy of investigation.

Cortical electrical activity has been the primary, if not sole source of signals for visual or automated detection and quantification of seizures in clinical use. The inextricable link between brain and epilepsy has historically impelled clinical neuroscientists to leave unexploited the equally inextricable link between brain and body. The brain-epilepsy link has distracted attention from certain limitations inherent to the recording of cortical signals from scalp or even directly from its surface. These limitations of brain-based approaches to seizure detection include marked cortical signal attenuation and filtering, and limited access to neural sources (only about one-third of the neocortex is surveyable by scalp electrodes; subdural electrodes record little activity from the lateral and bottom walls of sulci). Yet, readily accessible sources that provide indirect but valuable information about the state of the brain, particularly during the ictal or postictal state, remain largely untapped.

The growing emphasis on widely accessible, cost-effective, good quality health care in the context of expanding populations, especially in age-groups above 60 yr. in whom the incidence of epilepsy is high, and the shrinking financial resources to support the required infra-structure, pose an enormous challenge to patients whose seizures are pharmaco-resistant as well as to epileptologists and functional neurosurgeons. The emphasis on implantable intracranial devices for automated seizure detection, warning and delivery of therapy in patients with drug-resistant seizures should be viewed in the context that even if economic resources were unlimited, human resources are starkly small. Given the number of functional neurosurgeons in the United States (one source puts the number at 300, of which about 100 work in epilepsy) is it realistic to pursue exclusively intracranial devices to address the unmet needs of pharmaco-resistant patients, conservatively estimated (in the US) at 600,000? The deleterious medical, and psycho-social impact of intractable epilepsy and its high cost of care, along with the sophisticated human and technological resources needed to address them, qualifies this, in these authors opinions, as a public health care problem. Indeed, scientific advances regardless of their value may not translate into improved care of epilepsy and lessen its burden, unless devices are broadly accessible; in short the challenge of ameliorating the global burden of drug-resistant epilepsies may exceed scientific and technological ones. If the answer to the question put forth a few lines above is in the negative (intracranial devices will not meet the global burden) viable alternatives must be sought.

The utilization of certain extra-cerebral signals looms as one such alternative. Cardiac (e.g., heart rate, EKG morphology) and motor (speed, direction and force of joint movements) signals are prime candidates for the following reasons: 1. Structures that form part of the central autonomic nervous system or are strongly interconnected with it, are common sites of epileptogenesis (e.g., amygdalae-hippocampi); 2. Spread of seizures out of the primary epileptogenic zone, is prevalent in pharmaco-resistant patients so that even if the site of origin is not part of the central autonomic network, invasion of it by ictal activity is quite common; 3. Partial seizures particularly if complex, are characterized by either positive (e.g., motor automatisms, hypermotoric behavior, clonic/myoclonic activity, focal increase in anti-gravitatory muscle tone) or negative (e.g., motionless, focal loss of antigravitatory muscle tone) phenomena that are stereotypical across seizures originating from the same site and appear relatively early in the course of seizures; 4. Cardiac and motor signals are highly robust, easily recordable as they do not require implantable devices or development of ground breaking technology; EKG, actigraphs, 3-D accelerometers are widely available commercially and are considerably less costly than those required for use in the central nervous system (CNS); 5. Signals of cardiac and motor origin lack the high complexity or large dimensionality of those generated by the brain's cortex, are simpler to process and analyze, and are thus less computationally expensive. Ease of computation allows the use of simpler, smaller devices compared to those required for computation of cortical signals and as they use less power, battery recharging or replacements are less frequent; 6. The neurosurgical procedures and potential associated complications make implantable devices unappealing to a majority of pharmaco-resistant patients that responded to a survey.

Among the numerous extra-cerebral signals usable for seizure detection, cardiac, have been the most extensively investigated. Tachycardia is a common manifestation of partial seizures, occurring in almost 90% of seizures of mesial temporal origin and precedes electrographic (as determined with scalp electrodes) and clinical onset in the majority of these seizures. (Tachycardia invariably occurs in primarily/secondarily generalized tonic-clonic seizures being higher in magnitude and longer duration than in partial seizures. Tachycardia with tonic-clonic seizures is multifactorial: neurogenic, metabolic, and exertional.) From a cardiac rhythm perspective, the increases in heart rate temporally correlated with seizures are rarely pathologic, being of sinus origin; additionally their magnitude is unlikely to compromise cardiac output in healthy individuals. Ictal tachycardia has a strong neurogenic component reflective of either an increase in sympathetic or withdrawal of parasympathetic activity; while increases in motor activity in reference to the interictal state would augment its magnitude, tachycardia occurs in subjects in whom seizures manifest with motionless. Bradycardia also occurs with seizures, albeit with much lower prevalence than tachycardia; so called "temporal lobe syncope", denoting the loss of consciousness (without convulsive activity) during partial seizures is caused by profound bradycardia.

In light of the potential to apply cardiac signals, and in particular of exploiting changes in heart rate (increases or decreases relative to an interictal baseline) for automated seizure detection, algorithms are being developed and tested to this end. In addition to detection and warning of seizures, heart rate changes may be used to quantify: a) Relative duration defined as the time said changes spend above or below an interictal reference value(s); b) Relative intensity corresponding to the area under the curve or to the product of peak/bottom heart rate and duration (in sec.); c) Seizure frequency/unit time (e.g., month). The challenge of this detection modality for ambulatory clinical applications, is the ubiquitousness of heart rate changes with daily life activities that may translate into large numbers of false positive detections. Arousal from sleep, standing up from a recumbent position, climbing stairs, are but a few of the myriad daily life activities associated with relative or absolute changes (e.g., increases) in heart rate. The discriminating power or positive predictive value (ictal vs. exertional) of this detection modality is currently the subject of investigation in epilepsy monitoring units. Heart rate, among other (rate of change/slope; P-QRS-T morphology) markers, during seizures, are recorded, analyzed and compared to those associated with protocolized motor activities (e.g., walking on a treadmill). Preliminary results show that the magnitude of ictal increases in heart rate is sufficiently large compared to non-strenuous exercises, so as to allow accurate differentiation and, consequently, detection of certain types of partial seizures. It would be naïve and incorrect to presume that univariate (e.g., heart rate changes alone) automated detection of seizures would yield worthwhile positive predictive power (PPV=number of true positive detections/total number of detections) in ambulatory patients. Multivariate-based detection would be required to achieve satisfactory performance in a sufficiently large number of patients; ictal (reversible) changes in EKG morphology while less prevalent than in heart rate, have higher specificity and may increase considerably speed of detection (e.g., to within 3 heart beats). Visual analysis of peri-ictal R-R plots, has led to the discovery of heart rate patterns with characteristic morphology that are reproducible among seizures sharing a common epileptogenic zone and appear to be a specific ictal marker. One of these patterns resembles the letter "M" and indicates heart rate changes during seizures may not be unidirectional or monotonic: in this example, heart rate elevation is followed by a return towards its interictal baseline, which in turn gives way to a second elevation in rate. These fluctuations may be attributable, in part to the co-existence of parasympathetic and cholinergic neurons within the same autonomic nervous system structure; specifically, components of the central autonomic network such as the Dorsal Medial Hypothalamus, the Paraventricular Nucleus of the hypothalamus and the Nucleus Tractus Solitarius have dual cholinergic and noradrenergic innervation. Heart rate changes are also expected to be dependent on time of day (circadian), level of consciousness (awake vs. asleep), patient's fitness level, activity level (walking vs. jogging), and emotional and cognitive states, as well as on ingestion of drugs with adrenergic or cholinergic actions.

Ictal motor activity (movement amplitude, direction, velocity and type and number of muscles groups involved) recorded with actigraphs/3-D accelerometers would enhance specificity of cardiac-based detection, as it is stereotypical across seizures originating from the same structure(s). Use of ictal motor movements to detect seizures independent of heart rate or other sensors is actively under investigation. For example, a wrist accelerometer accurately detected seven of eight tonic-clonic seizures, and nonseizure movements were readily identified by patients thereby reducing the consequence of false detections. As wearable technologies advance, so do opportunities for more precise measurement of complicated seizure-related movements such as automatisms.

Respiratory rate is markedly increased (also a neurogenic phenomenon) during seizures manifesting with tachycardia, and its specificity may be higher than heart rate changes as its magnitude and pattern differ amply from exertional increases in ventilation. Electrodermal (e.g. skin resistance, sudomotor) or vocal (e.g., non-formed vocalizations) activity, eyelid and ocular movements (gaze deviation, nystagmus), metabolic (e.g., profound normokalemic lactic acidosis with convulsions, hormonal (prolactin elevations with convulsion or certain partial seizures) or tissue stress (lactic acid, CK) indices may aid in extracerebral seizure detection.

Paradoxically, a potentially important hurdle in the path to adoption of extra-cerebral detection of seizures is the markedly low sensitivity and other limitations of patient diaries, the universal "gold" metric or "ground truth" in epileptology. The rate of automated seizure detection, whether cerebrally or extra-cerebrally based, will be higher, possibly much higher in certain cases, than obtainable with diaries as not only clinical, but also "subclinical" seizures will be logged. This "limitation" or "inconvenience" that may discourage patients and epileptologists, is compounded by the absence of simultaneously recorded cortical activity, since direct proof cannot be furnished that a change in extra-cerebral indices, was indeed caused by a seizure. A simple, but powerful means to overcome this hurdle is through the administration of complex reaction time tests implementable in real-time, into hand-held devices and triggered by changes in extra-cerebral signals such as EKG; in a cooperative, motivated patient, cardiac activity changes in the context of an abnormal response or failed test will be classified as clinical seizures, while those with a preserved response as either subclinical seizures or false positive detections.

Based on the existing evidence and body or work, it may be stated that extra-cerebral automated detection, warning, logging of seizures and delivery of therapy, looms as a useful, cost-effective and widely accessible option to better manage pharmaco-resistant epilepsies.

An embodiment of a medical device adaptable for use in implementing some aspects of embodiments of the present invention is provided in FIG. 1. As shown in FIG. 1, a system may involve a medical device system that senses body signals of the patient—such as brain or cardiac activity—and analyzes those signals to identify one or more aspects of the signal that may identify the occurrence of a seizure. The signal may be processed to extract (e.g., mathematically by an algorithm that computes certain values from the raw or partially processed signal) features that may be used to identify a seizure when compared to the inter-ictal state. As shown in the right side of FIG. 1, the features may also be graphically displayed either in real time or subsequent to the event to enable visual confirmation of the seizure event and gain additional insight into the seizure (e.g., by identifying a seizure metric associated with the seizure).

Figure 2:
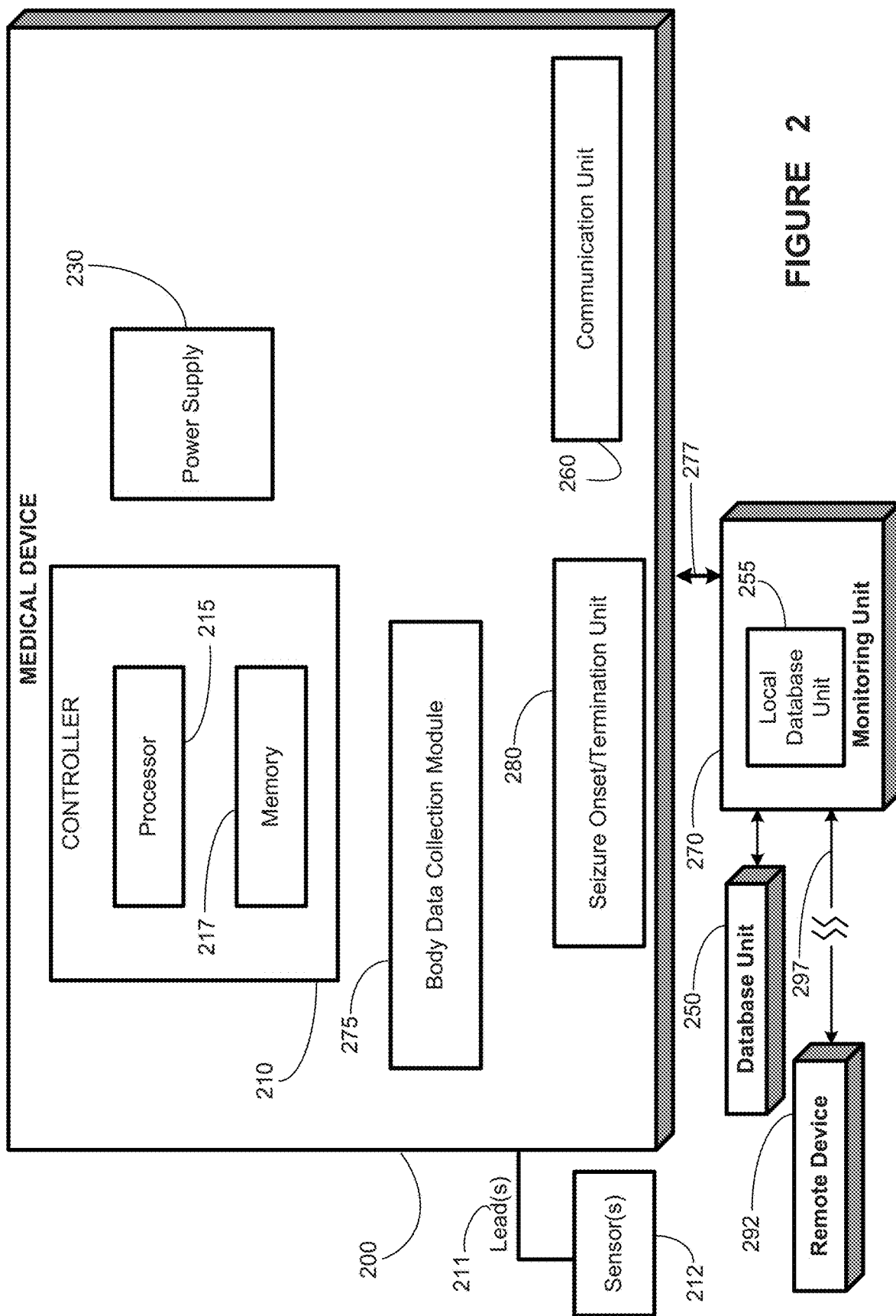
FIG. 2 illustrates a medical device system, according to an illustrative embodiment of the present disclosure.

Turning now to FIG. 2, a block diagram depiction of a medical device 200 is provided, in accordance with one illustrative embodiment of the present invention. In some embodiments, the medical device 200 may be implantable, while in other embodiments the medical device 200 may be completely external to the body of the patient.

The medical device 200 may comprise a controller 210 capable of controlling various aspects of the operation of the medical device 200. The controller 210 is capable of receiving internal data or external data, and in one embodiment, is capable of causing a therapy unit (not shown) to generate and deliver a therapy, such as an electrical signal, a drug, a cooling therapy, or two or more thereof, to one or more target tissues of the patient's body for treating a medical condition. Controller 210 may receive manual instructions from an operator externally, and may cause a therapy to be generated and delivered based on internal calculations and programming. In other embodiments, the medical device 200 does not comprise a therapy unit. In either embodiment, the controller 210 is capable of affecting substantially all functions of the medical device 200.

The controller 210 may comprise various components, such as a processor 215, a memory 217, etc. The processor 215 may comprise one or more microcontrollers, microprocessors, etc., capable of performing various executions of software components. The memory 217 may comprise various memory portions where a number of types of data (e.g., internal data, external data instructions, software codes, status data, diagnostic data, etc.) may be stored. The memory 217 may comprise one or more of random access memory (RAM), dynamic random access memory (DRAM), electrically erasable programmable read-only memory (EEPROM), flash memory, etc.

The medical device 200 may also comprise a power supply 230 which may comprise a battery, voltage regulators, capacitors, etc., to provide power for the operation of the medical device 200, including electronic operations and therapy generation and delivery functions. The power supply 230 may be rechargeable or non-rechargeable. Different kinds of power supplies may be suitable for use in particular embodiments of the medical device 200, such as a lithium/thionyl chloride cell or a lithium/carbon monofluoride (LiCFx) cell if the medical device 200 is implantable, or conventional watch or 9V batteries for external (i.e., non-implantable) embodiments. Other battery types known in the art of medical devices may also be used.

The medical device 200 may also comprise a communication unit 260 capable of facilitating communications between the medical device 200 and various other devices. In particular, the communication unit 260 is capable of providing transmission and reception of electronic signals to and from a monitoring unit 270, such as a handheld computer or PDA that can communicate with the medical device 200 wirelessly or by cable. The communication unit 260 may include hardware, software, firmware, or any combination thereof.

The medical device 200 may also comprise one or more sensor(s) 212 coupled via sensor lead(s) 211 to the medical device 200. The sensor(s) 212 are capable of receiving signals related to a body signal, such as the patient's heart beat, blood pressure, and/or temperature, and delivering the signals to the medical device 200. The sensor 212 may also be capable of detecting kinetic signal associated with a patient's movement. The sensor 212, in one embodiment, may be an accelerometer. The sensor 212, in another embodiment, may be an inclinometer. In another embodiment, the sensor 212 may be an actigraph. In one embodiment, the sensor(s) 212 may be electrode(s) capable of also providing an electrical stimulation therapy. In other embodiments, the sensor(s) 212 are external structures that may be placed on the patient's skin, such as over the patient's heart or elsewhere on the patient's torso, for detecting heart rate, blood pressure, blood oxygen saturation, skin resistivity, skin temperature, and other externally detectable body signals. The sensor 212, in one embodiment is a multimodal signal sensor capable of detecting various autonomic and neurologic signals, including kinetic signals associated with the patient's movement.

The seizure onset/termination unit 280 is capable of detecting an epileptic event based upon one or more signals provided by body data collection module 275. The seizure onset/termination unit 280 can implement one or more algorithms (e.g., a PMSA algorithm, an autoregression algorithm, a WTMM algorithm, or a STA/LTA algorithm) using the autonomic data and neurologic data in any particular order, weighting, etc. The seizure onset/termination unit 280 may comprise software module(s) that are capable of performing various interface functions, filtering functions, etc. In another embodiment, the seizure onset/termination unit 280 may comprise hardware circuitry that is capable of performing these functions. In yet another embodiment, the seizure onset/termination unit 280 may comprise hardware, firmware, software and/or any combination thereof.

In addition to components of the medical device 200 described above, a medical device system may comprise a storage unit to store an indication of a seizure detection by seizure onset/termination unit 280. The storage unit may be the memory 217 of the medical device 200, another storage unit of the medical device 200, or an external database, such as a local database unit 255 or a remote database unit 250. The medical device 200 may communicate the indication via the communications unit 260. Alternatively or in addition to an external database, the medical device 200 may be adapted to communicate the indication to at least one of a patient, a caregiver, or a healthcare provider.

In various embodiments, one or more of the units or modules described above may be located in a monitoring unit 270 or a remote device 292, with communications between that unit or module and a unit or module located in the medical device 200 taking place via communication unit 260. For example, in one embodiment, one or more of the body data collection module 275 or the seizure onset/termination unit 280 may be external to the medical device 200, e.g., in a monitoring unit 270. Locating one or more of the body data collection module 275 or the seizure onset/termination unit 280 outside the medical device 200 may be advantageous if the calculation(s) is/are computationally intensive, in order to reduce energy expenditure and heat generation in the medical device 200 or to expedite calculation.

The monitoring unit 270 may be a device that is capable of transmitting and receiving data to and from the medical device 200. In one embodiment, the monitoring unit 270 is a computer system capable of executing a data-acquisition program. The monitoring unit 270 may be controlled by a healthcare provider, such as a physician, at a base station in, for example, a doctor's office. In alternative embodiments, the monitoring unit 270 may be controlled by a patient in a system providing less interactive communication with the medical device 200 than another monitoring unit 270 controlled by a healthcare provider. Whether controlled by the patient or by a healthcare provider, the monitoring unit 270 may be a computer, preferably a handheld computer or PDA, but may alternatively comprise any other device that is capable of electronic communications and programming, e.g., hand-held computer system, a PC computer system, a laptop computer system, a server, a personal digital assistant (PDA), an Apple-based computer system, a cellular telephone, etc. The monitoring unit 270 may download various parameters and program software into the medical device 200 for programming the operation of the medical device, and may also receive and upload various status conditions and other data from the medical device 200. Communications between the monitoring unit 270 and the communication unit 260 in the medical device 200 may occur via a wireless or other type of communication, represented generally by line 277 in FIG. 2. This may occur using, e.g., a wand to communicate by inductive or RF energy with medical device 200. Alternatively, the wand may be omitted in some systems, e.g., systems in which the MD 200 is non-implantable, or implantable systems in which monitoring unit 270 and MD 200 operate in the MICS bandwidths.

In one embodiment, the monitoring unit 270 may comprise a local database unit 255. Optionally or alternatively, the monitoring unit 270 may also be coupled to a database unit 250, which may be separate from monitoring unit 270 (e.g., a centralized database wirelessly linked to a handheld monitoring unit 270). The database unit 250 and/or the local database unit 255 are capable of storing various patient data. These data may comprise patient parameter data acquired from a patient's body, therapy parameter data, seizure severity data, and/or therapeutic efficacy data. The database unit 250 and/or the local database unit 255 may comprise data for a plurality of patients, and may be organized and stored in a variety of manners, such as in date format, severity of disease format, etc. The database unit 250 and/or the local database unit 255 may be relational databases in one embodiment. A physician may perform various patient management functions (e.g., programming parameters for a responsive therapy and/or setting references for one or more detection parameters) using the monitoring unit 270, which may include obtaining and/or analyzing data from the medical device 200 and/or data from the database unit 250 and/or the local database unit 255. The database unit 250 and/or the local database unit 255 may store various patient data.

One or more of the blocks illustrated in the block diagram of the medical device 200 in FIG. 2 may comprise hardware units, software units, firmware units, or any combination thereof. Additionally, one or more blocks illustrated in FIG. 2 may be combined with other blocks, which may represent circuit hardware units, software algorithms, etc. Additionally, any number of the circuitry or software units associated with the various blocks illustrated in FIG. 2 may be combined into a programmable device, such as a field programmable gate array, an ASIC device, etc.

Figure 3:
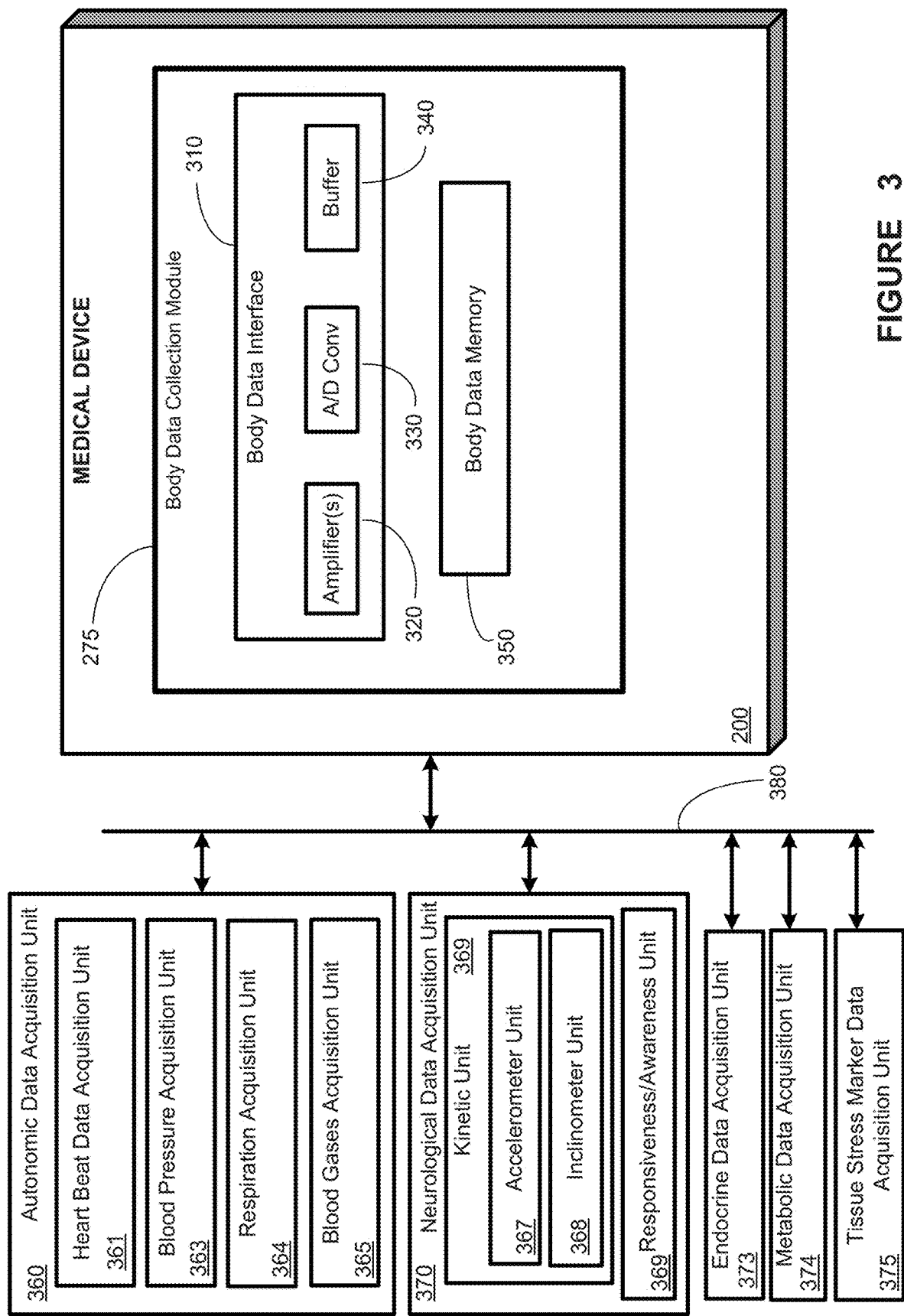
FIG. 3 provides a stylized diagram of a medical device and different data acquisition units that may provide output(s) used by other unit(s) of the medical device, in accordance with one illustrative embodiment of the present disclosure.

Turning now to FIG. 3, a block diagram depiction of an exemplary implementation of the body data collection module 275 is shown. The body data collection module 275 may include hardware (e.g., amplifiers, accelerometers), tools for chemical assays, optical measuring tools, a body data memory 350 (which may be independent of memory 117 or part of it) for storing and/or buffering data. The body data memory 350 may be adapted to store body data for logging or reporting and/or for future body data processing and/or statistical analyses. Body data collection module 275 may also include one or more body data interfaces 310 for input/output (I/O) communications between the body data collection module 275 and sensors 112. Body data from memory 350 and/or interface 310 may be provided to one or more body index calculation unit(s) 355, which may determine one or more body indices.

In the embodiments of FIG. 3, sensors 112 may be provided as any of various body data units/modules (e.g., autonomic data acquisition unit 360, neurological data acquisition unit 370, endocrine data acquisition unit 373, metabolic data acquisition unit 374, tissue stress marker data acquisition unit 375, and physical fitness/integrity determination unit 376) via connection 380. Connection 380 may be a wired connection (e.g., a lead) a wireless connection, or a combination of the two. Connection 380 may be a bus-like implementation or may include an individual connection (not shown) for all or some of the body data units.

In one embodiment, the autonomic data acquisition unit 360 may include a cardiac data acquisition unit 361 adapted to acquire a phonocardiogram (PKG), EKG, echocardiography, apexcardiography and/or the like, a blood pressure acquisition unit 363, a respiration acquisition unit 364, a blood gases acquisition unit 365, and/or the like. In one embodiment, the neurologic data acquisition unit 370 may contain a kinetic unit 366 that may comprise an accelerometer unit 367, an inclinometer unit 368, and/or the like; the neurologic data acquisition unit 370 may also contain a responsiveness/awareness unit 369 that may be used to determine a patient's responsiveness to testing/stimuli and/or a patient's awareness of their surroundings. Body data collection module 275 may collect additional data not listed herein, that would become apparent to one of skill in the art having the benefit of this disclosure.

The body data units ([360-370], [373-377]) may be adapted to collect, acquire, receive/transmit heart beat data, EKG, PKG, echocardiogram, apexcardiogram, blood pressure, respirations, blood gases, body acceleration data, body inclination data, EEG/ECoG, quality of life data, physical fitness data, and/or the like.

The body data interface(s) 310 may include various amplifier(s) 320, one or more A/D converters 330 and/or one or more buffers 340 or other memory (not shown). In one embodiment, the amplifier(s) 320 may be adapted to boost and condition incoming and/or outgoing signal strengths for signals such as those to/from any of the body data acquisition units/modules (e.g., ([360-370], [373-377])) or signals to/from other units/modules of the MD 100. The A/D converter(s) 330 may be adapted to convert analog input signals from the body data unit(s)/module(s) into a digital signal format for processing by controller 210 (and/or processor 215). A converted signal may also be stored in a buffer(s) 340, a body data memory 350, or some other memory internal to the MD 100 (e.g., memory 117, FIG. 1) or external to the MD 100 (e.g., monitoring unit 170, local database unit 155, database unit 150, and remote device 192). The buffer(s) 340 may be adapted to buffer and/or store signals received or transmitted by the body data collection module 275.

As an illustrative example, in one embodiment, data related to a patient's respiration may be acquired by respiration unit 364 and sent to MD 100. The body data collection module 275 may receive the respiration data using body data interface(s) 310. As the data is received by the body data interface(s) 310, it may be amplified/conditioned by amplifier(s) 320 and then converted by A/D converter(s) into a digital form. The digital signal may be buffered by a buffer(s) 340 before the data signal is transmitted to other components of the body data collection module 275 (e.g., body data memory 350) or other components of the MD 100 (e.g., controller 110, processor 115, memory 117, communication unit 160, or the like). Body data in analog form may be also used in one or more embodiments.

Body data collection module 275 may use body data from memory 350 and/or interface 310 to calculate one or more body indices in body one or more body index calculation unit(s) 355. A wide variety of body indices may be determined, including a variety of autonomic indices such as heart rate, blood pressure, respiration rate, blood oxygen saturation, neurological indices such as maximum acceleration, patient position (e.g., standing or sitting), and other indices derived from body data acquisition units 360, 370, 373, 374, 375, 376, 377, etc.

Figure 4:
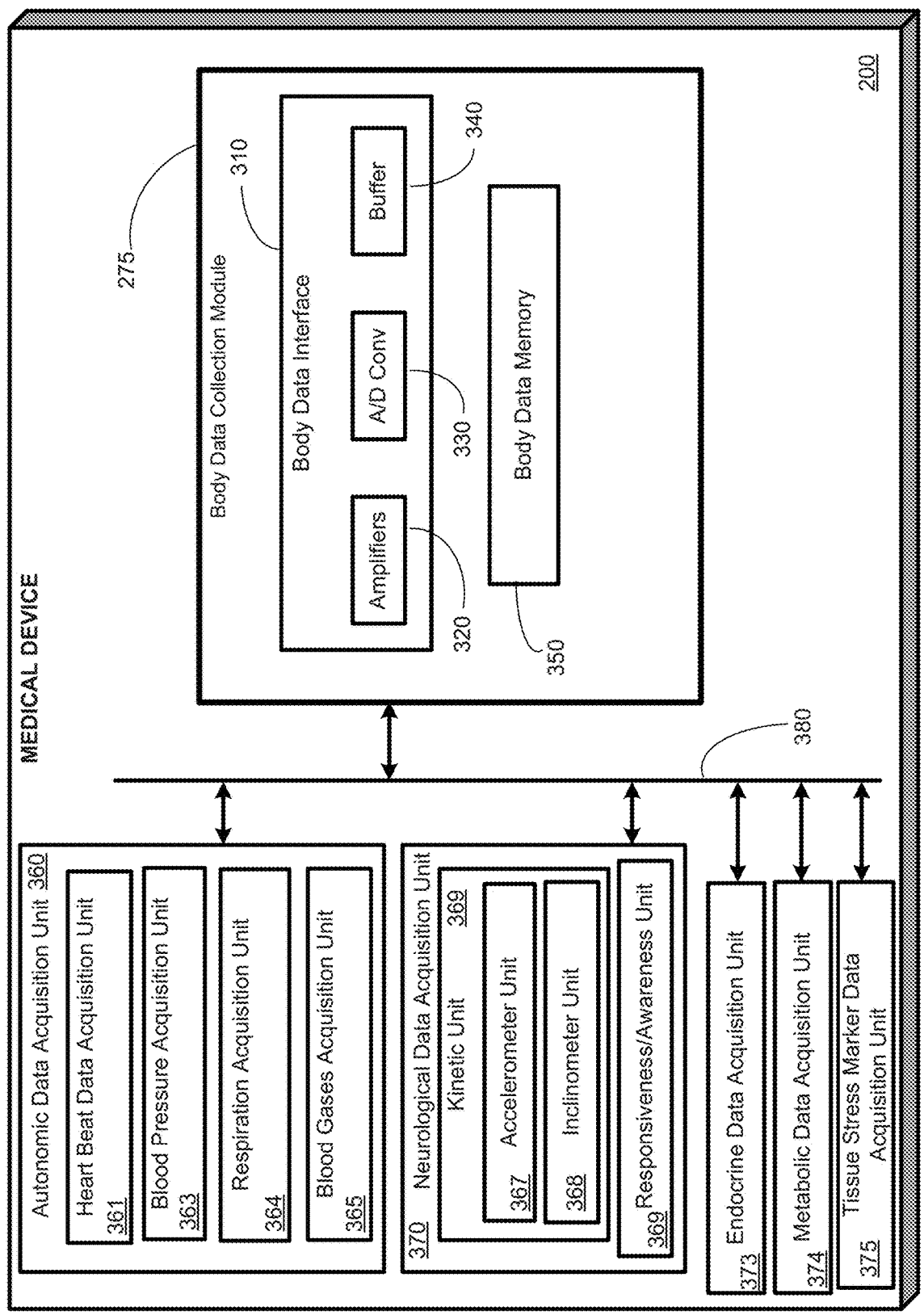
FIG. 4 provides a stylized diagram of a medical device and different data acquisition units that may provide output(s) used by other unit(s) of the medical device, in accordance with one illustrative embodiment of the present disclosure.

Turning now to FIG. 4, an MD 100 (as described in FIG. 3) is provided, in accordance with one illustrative embodiment of the present invention. FIG. 4 depicts the body data acquisition units similar to those shown in FIG. 3, in accordance with another embodiment, wherein these unites are included within the MD 100, rather being externally coupled to the MD 100, as shown in FIG. 3. In accordance with various embodiments, any number and type of body data acquisition units may be included within the MD 100, as shown in FIG. 4, while other body data units may be externally coupled, as shown in FIG. 3. The body data acquisition units may be coupled to the body data collection module 275 in a fashion similar to that described above with respect to FIG. 3, or in any number of different manners used in coupling intra-medical device modules and units. The manner by which the body data acquisition units may be coupled to the body data collection module 275 is not essential to, and does not limit, embodiments of the instant invention as would be understood by one of skill in the art having the benefit of this disclosure. Embodiments of the MD depicted in FIG. 4 may be fully implantable or may be adapted to be provided in a system that is external to the patient's body.

A time series body signal collected by the body data collection module 275 may comprise at least one of a measurement of the patient's heart rate, a measurement of the patient's kinetic activity, a measurement of the patient's brain electrical activity, a measurement of the patient's oxygen consumption, a measurement of the patient's work, a measurement of an endocrine activity of the patient, a measurement of a metabolic activity of the patient, a measurement of an autonomic activity of the patient, a measurement of a cognitive activity of the patient, or a measurement of a tissue stress marker of the patient.

Figure 5:
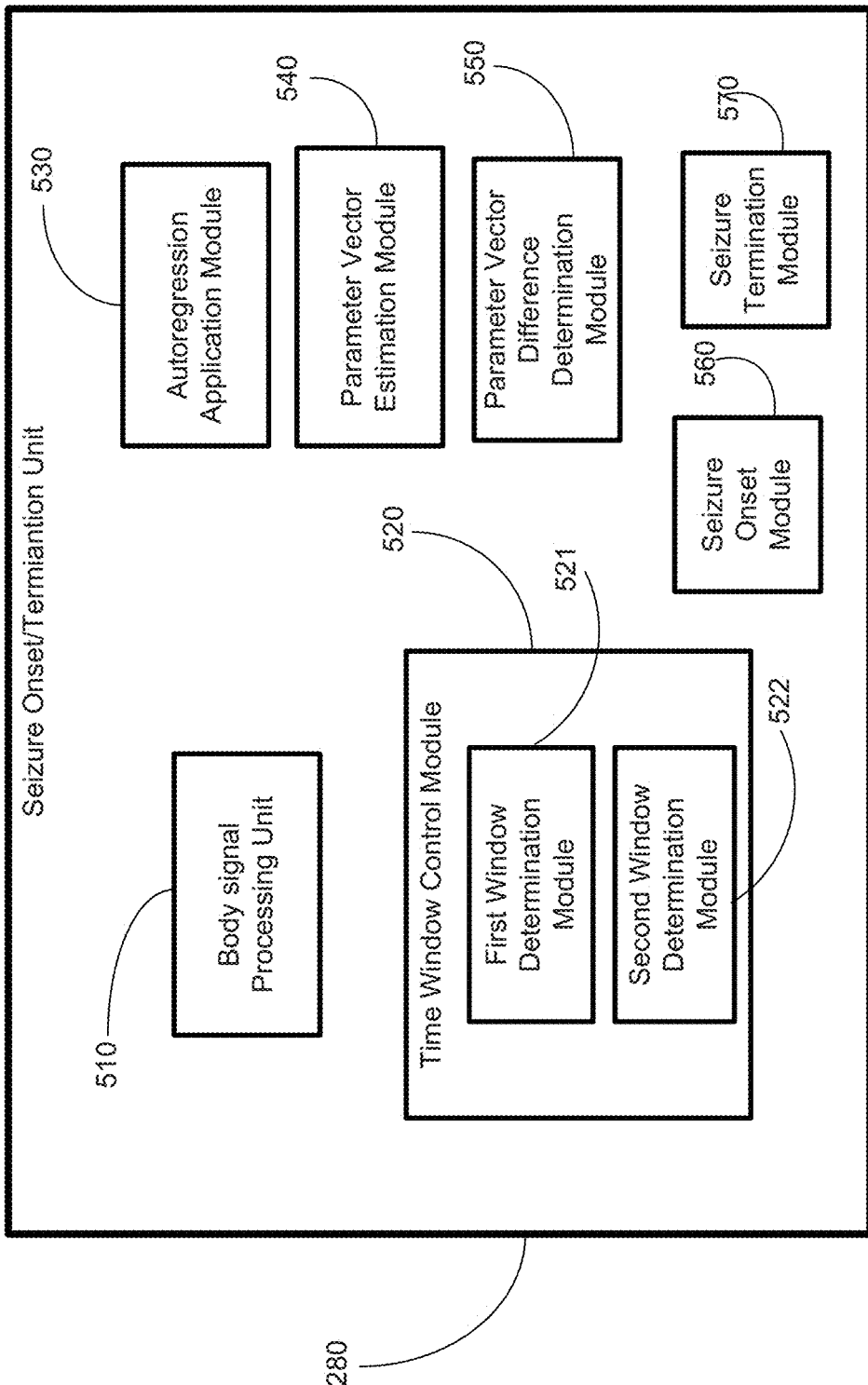
FIG. 5 provides a stylized diagram of a seizure onset/termination unit, in accordance with one illustrative embodiment of the present disclosure.

Turning to FIG. 5, the seizure onset/termination unit 280 depicted in FIG. 2 is shown in greater detail. The seizure onset/termination unit 280 may comprise a body signal interface 510 adapted to received collected body data from the body data collection module 275 and detect a seizure by identification of an onset time and a seizure termination time. For example, the seizure onset/termination unit 280 may be adapted to receive a time series of collected body data.

The seizure onset/termination unit 280 may also comprise a time window control module 520. The time window control module 520 may comprise a first window determination module 521, adapted to determine a sliding time window for the time series body signal comprising a first window; and/or a second window determination module 522, adapted to determine a sliding time window for the time series body signal comprising a second window.

In other embodiments (not shown), any time window used herein may be a moving time window, not necessarily a sliding time window. As used herein, a "sliding" time window moves over continuous points of a time series and the present (e.g., foreground) and past (e.g., background) are contiguous in time, if not overlapping. For example, if the foreground window is 5 s and the background 60 s in length, and the current time is 10:00:00 AM, the temporal location of the foreground window may be 10:00:00-10:00:05 and that of the background, 09:59:00-10:00:00. A "moving" time window may move over continuous points of the time series or "jump" over discontinuous points. For example, a moving window may be chosen from past data that optimizes sensitivity, specificity, or speed of detection as required by the patient's prevailing conditions, activities, or time of day, said time being discontiguous from that of the foreground window. Using the example cited immediately above, in this example, the foreground window of 5 s at 10:00:00 AM may be compared to a 60 s background recorded 6 hr. earlier (04:00:00-04:01:00). A moving window may also be the average or median of several windows.

The seizure onset/termination unit 280 may also comprise an autoregression application module 530. The autoregression application module 530 may be adapted to apply an autoregression algorithm to each of the first and second time windows, to yield an autoregression coefficient for each window and a residual variance for each window.

The autogression model may be of second order, and have parameters comprising a second time window length of 1 second; a first time window length of 1 second; and a detection threshold (R) of 3.

The parameters of the autogression model may be selected based on at least one of a clinical application of said detection; a level of safety risk associated with an activity; at least one of an age, physical state, or mental state of the patient; a length of a window available for warning; a degree of efficacy of therapy and of its latency; a degree of seizure control; a degree of circadian and ultradian fluctuations of said patient's seizure activity; a performance of the detection method as a function of the patient's sleep/wake cycle or vigilance level; a dependence of the patient's seizure activity on at least one of a level of consciousness, a level of cognitive activity, or a level of physical activity; the site of seizure origin; a seizure type suffered by said patient; a desired sensitivity of detection of a seizure, a desired specificity of detection of a seizure, a desired speed of detection of a seizure, an input provided by the patient, or an input provided by a sensor.

In various embodiments, the selected parameters may reflect the degree of certainty of detections desired by the patient, a caregiver, a medical professional, or two or more thereof. Such person(s) are expected to have biases regarding their desire for certainty of detection, and variation in their risk-proneness and/or aversion to risk. Thus, in one embodiment, the patient, caregiver, and/or medical professional may be allowed to change (within certain limits and for certain activities only, if desired) the sensitivity, specificity, and/or speed of detection of the algorithms.

The seizure onset/termination unit 280 may also comprise a parameter vector estimation module 540. The parameter vector estimation module 540 may be adapted to estimate a parameter vector for each of the first and second windows, based at least in part on the autoregression coefficients and the residual variances determined by the autoregression application module 530.

The seizure onset/termination unit 280 may also comprise a parameter vector difference determination module 550. The parameter vector difference determination module 550 may be adapted to determine a difference of the parameter vectors for each of the first and second windows. For example, the parameter vector difference determination module 550 may implement a matrix function to determine the difference.

The seizure onset/termination unit 280 may also comprise a seizure onset determination module 560. The seizure onset determination module 560 may be configured to determine an onset of a seizure based on the difference between the parameter vectors. For example, the seizure onset determination module 560 may determine a seizure onset if the difference indicates a larger variance in the first window than in the second window.

The seizure onset/termination unit 280 may also comprise a seizure termination determination module 570. The seizure termination determination module 570 may be adapted to determine a termination of a seizure based on the difference between the parameter vectors. For example, the seizure termination determination module 570 may determine a seizure termination if the difference indicates a larger variance in the second window than in the first window.

Figure 10:
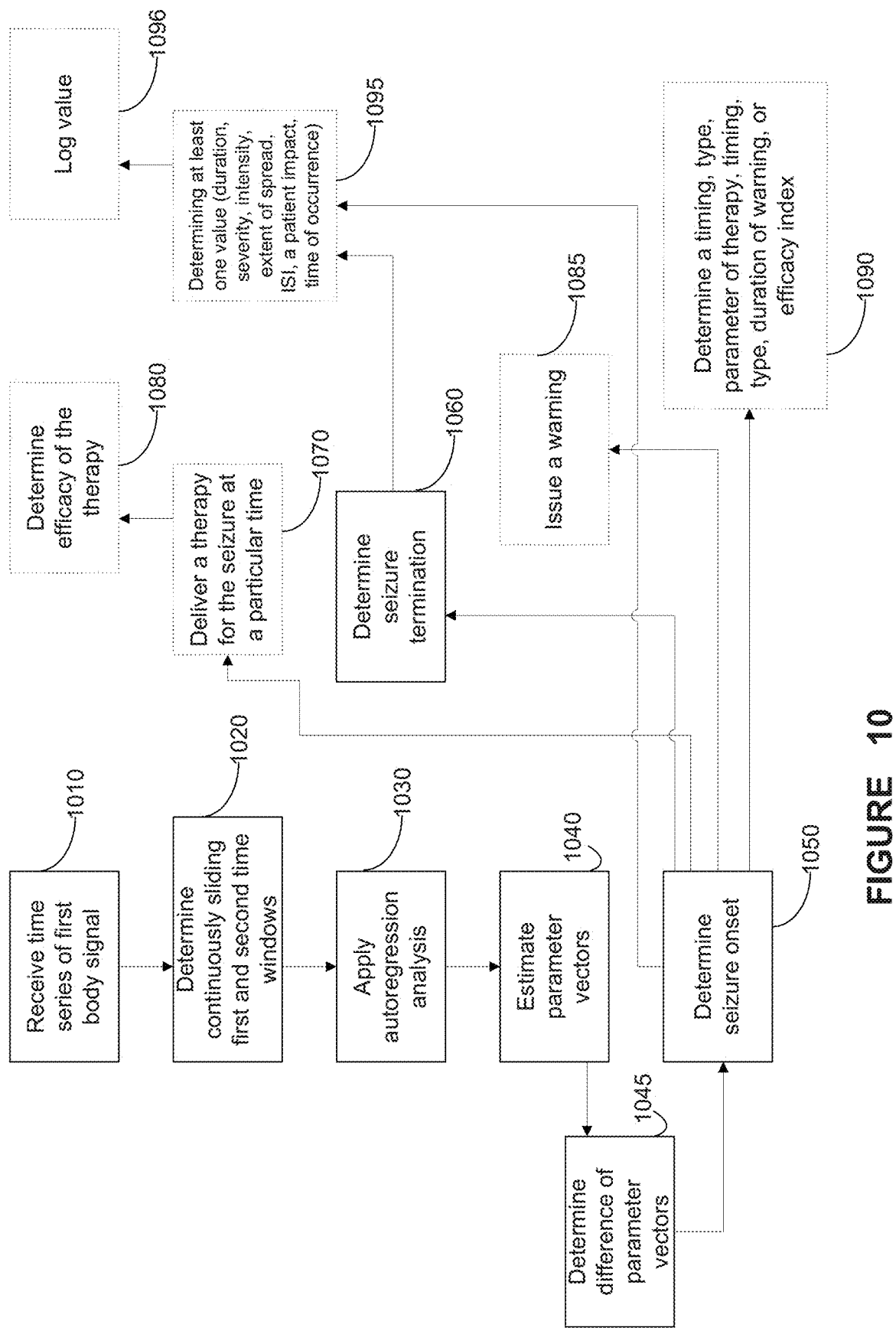
FIG. 10 provides a flowchart depiction of a method, in accordance with one illustrative embodiment of the present disclosure.

Turning to FIG. 10, a flowchart depiction of a method for detecting an onset and a termination of an epileptic event from a patient body signal is shown. A time series of a first body signal of a patient may be received at 1010. Sliding first and second time windows for the time series body signal may be determined at 1020. An autoregression algorithm may then be applied, such as by applying an autoregression analysis at 1030 to each of the first and second windows to yield a plurality of autoregression coefficients and a residual variance for each window. A parameter vector may then be estimated at 1040 for each of the first and second windows, based at least in part on the autoregression coefficients and the residual variances. A difference between the parameter vectors may be determined at 1045. For example, the difference may be determined at 1045 by use of a matrix function. An onset of a seizure may be determined at 1050 based on the difference between the parameter vectors, for example, if the difference indicates a larger variance in the second window than in the first window. A termination of a seizure may be determined at 1060 based on the difference between the parameter vectors, for example if the difference indicates a larger variance in the first window than in the second window.

Optionally, the method depicted in FIG. 10 may comprise other activities. The method may further involve delivering a therapy for the seizure at a particular time at 1070, wherein at least one of the therapy, the particular time, or both is based upon the determination of the seizure onset.

Alternatively or in addition, the method may further involve determining at 1080 an efficacy of the therapy.

Alternatively or in addition, the method may further involve issuing at 1085 a warning for the seizure, wherein the warning is based upon the determination of the seizure onset.

Alternatively or in addition, at least one of the delivered therapy or the issued warning may be based at least in part on at least one of the type of activity engaged in by the patient at the time of seizure onset, the seizure type, the seizure severity, or the time elapsed from the last seizure.

Alternatively or in addition, the method may further involve determining at 1090 at least one of a timing of delivery of therapy, a type of therapy, at least one parameter of the therapy, a timing of sending a warning, a type of warning, a duration of the warning, or an efficacy of said therapy, based upon a timing of said determination of said seizure onset, said determination of said seizure termination, or both.

Alternatively or in addition, the method may further involve determining at 1095 at least one value selected from the duration of the epileptic event, the severity of the epileptic event, the intensity of the epileptic event, the extent of spread of the epileptic event, an inter-seizure interval between the epileptic event and a prior epileptic event, a patient impact of the epileptic event, or a time of occurrence of the epileptic event. The method may further comprise logging at 1096 at least one data point associated with the seizure, such as a time of occurrence of the seizure, a seizure duration, a seizure severity, a type of therapy and/or time of delivery thereof, etc.

A method, such as that depicted in FIG. 10, may be implemented by a non-transitory computer readable program storage unit encoded with instructions that, when executed by a computer, perform the method.

An activity, such as walking, swimming, driving, etc., may be allowed or terminated, a warning may be issued or not issued, or a therapy may be delivered or not delivered, based on the determination of seizure onset, seizure termination, or both, either for the autoregression algorithm alone or a PMSA value calculated at least in part from an indicator function derived from the autoregression algorithm.

An "efficacy index" may be used herein to refer to any quantification of an efficacious result of a therapy. In one example, if a patient's seizures typically present an increase in heart rate from a resting rate of 80 beats per minute (BPM) to a peak ictal heart rate of 160 BPM, and upon administering a therapy to the patient, the patient's peak ictal heart rate is 110 BPM, this result may be quantified as an efficacy index of 50 (on a scale of non-therapy peak ictal heart rate-peak ictal heart rate after therapy), 0.625 (50 BPM reduction from peak ictal heart rate/80 BPM increase from resting rate to peak ictal heart rate in the absence of therapy), etc.

What is claimed:

1. A non-transitive, computer-readable storage device for storing data that when executed by one or more medical devices, performs a method, comprising:
receiving via the one or more medical devices a body signal of a patient during a first time series obtained from one or more sensors;
determining a movable first time window and a movable second time window for the first time series;
applying a spectral filter having a predetermined power spectral density to each of the movable first time window and the movable second time window;
determining a ratio of a spectral power between the movable first time window and the movable second time window;
determining a seizure onset in response to a first determination that the ratio reaches an onset threshold;
initiating an electrical therapy based on the seizure onset determination; and
determining a seizure termination in response to a second determination that the ratio reaches a termination threshold;
wherein at least one parameter selected from the movable foreground time window, the movable background time window, the spectral filter, the onset threshold, or the termination threshold is selected based on a reference value.

2. The non-transitive, computer-readable storage device of claim 1, including data that when executed by the one or more medical devices perform the method of claim 1, wherein:
the movable first time window comprises from eight to thirty-two samples ($N_{STA}$); and
the movable second time window comprises from 180 to 720 samples ($N_{LTA}$).

3. The non-transitive, computer-readable storage device of claim 1, including data that when executed by the one or more medical devices perform the method of claim 1, wherein
the movable first time window comprises 16 samples ($N_{STA}$);
the movable second time window comprises 360 samples ($N_{LTA}$);
a time of seizure onset ($T_{onset}$) corresponds to a time fulfilling a condition $STALTA(\tau+N_{STA}/2) \geq T_{onset}$, wherein $$STALTA(\tau) = \frac{\sum_{t=\tau-N_{STA}+1}^{\tau} X^2(t)/N_{STA}}{\sum_{t=\tau-N_{LTA}+1}^{\tau} X^2(t)/N_{LTA}}$$

and $\tau$ is a common right-hand end of both the movable first time window and the movable second time window;
a time of the seizure termination corresponds to a second time fulfilling a second condition of max $\{STALTA(s), \tau-N_{STA} \leq s \leq \tau\} \leq T_{end}$; and
a filter's spectral density corresponds to a Daubechies wavelet order 4, level 3.

4. The non-transitive, computer-readable storage device of claim 1, including data that when executed by the one or more medical devices perform the method of claim 1, wherein the first time series body signal comprises at least one of a measurement of a patient's heart rate, a measurement of a patient's physical activity, a measurement of a patient's oxygen consumption, or a measurement of a patient's work.

5. The non-transitive, computer-readable storage device of claim 1, including data that when executed by the one or more medical devices perform the method of claim 1, further comprising:

where initiating the electrical therapy includes delivering the electrical therapy for the seizure at a particular time, wherein at least one of the electrical therapy, the particular time of the electrical therapy delivery, or both is based upon the determination of the seizure onset and a seizure severity.

6. The non-transitive, computer-readable storage device of claim 5, including data that when executed by the one or more medical devices perform the method of claim 5, further comprising at least one of:

determining an efficacy of the electrical therapy; or issuing a warning for the seizure, wherein the warning is based upon the determination of the seizure onset and the seizure severity.

7. The non-transitive, computer-readable storage device of claim 1, including data that when executed by the one or more medical devices perform the method of claim 1, further comprising determining at least one of a timing of delivery of the electrical therapy, a type of the electrical therapy, at least one parameter of the electrical therapy, a timing of sending a warning, a type of the warning, a duration of the warning, or an efficacy index, based upon a timing of the determination of the seizure onset.

* * * * *